United States Patent [19]
Boissé et al.

[11] Patent Number: 5,613,963
[45] Date of Patent: Mar. 25, 1997

[54] NON-WOVEN PANTY LINER AND A METHOD AND APPARATUS FOR MANUFACTURING SAME

[75] Inventors: Sylvie Boissé, Anjou; Roger Boulanger, Ste-Julie, both of Canada; Joseph Israël, Belcheltown, Mass.

[73] Assignee: Johnson & Johnson Consumer Products, Inc., Skillman, N.J.

[21] Appl. No.: 376,545

[22] Filed: Jan. 23, 1995

Related U.S. Application Data

[63] Continuation of Ser. No. 54,331, Apr. 28, 1993, abandoned.
[51] Int. Cl.[6] .................................................. A61F 13/15
[52] U.S. Cl. ..................... 604/384; 604/365; 604/370; 604/378; 604/385.1
[58] Field of Search ............................. 604/358, 365, 604/366, 370–371, 378–385.1

[56] References Cited

U.S. PATENT DOCUMENTS

| | | |
|---|---|---|
| 2,862,251 | 12/1958 | Kalwaites . |
| 2,929,379 | 3/1960 | Poulsen ..................................... 604/372 |
| 3,860,002 | 1/1975 | Kolbach . |
| 3,934,588 | 1/1976 | Mesek et al. . |
| 4,129,132 | 12/1978 | Butterworth et al. . |
| 4,145,464 | 3/1979 | McConnell et al. . |
| 4,518,451 | 5/1985 | Luceri et al. . |
| 4,629,457 | 12/1986 | Ness ........................................ 604/370 |
| 4,704,112 | 11/1987 | Suzuki et al. . |
| 4,795,455 | 1/1989 | Luceri et al. ............................ 604/386 |
| 4,883,707 | 11/1989 | Newkirk . |

*Primary Examiner*—John G. Weiss
*Assistant Examiner*—P. Zuttarelli
*Attorney, Agent, or Firm*—James P. Barr

[57] ABSTRACT

A panty liner comprising a primary liquid-retaining component in the form of a unitary sheet of non-woven fabric. A liquid-impervious barrier layer is affixed to the sheet of non-woven fabric to prevent body exudate absorbed therein to egress through a garment facing side of the panty liner. The invention also extends to a method and to an apparatus for manufacturing the panty liner.

25 Claims, 10 Drawing Sheets
(1 of 10 Drawing(s) in Color)

NON-WOVEN PANTY LINER AND A METHOD AND APPARATUS FOR MANUFACTURING SAME

This is a continuation of application Ser. No. 08/054,331, filed Apr. 28, 1993, now abandoned.

FIELD OF THE INVENTION

The invention relates to the art of manufacturing disposable absorbent products, more particularly, to an improved panty liner made primarily of non-woven fibrous material. The invention also extends to a method and to an apparatus for manufacturing the aforementioned panty liner.

BACKGROUND OF THE INVENTION

To prevent garment staining as a result of occasional non-menstrual vaginal discharges, it is common practice to use a thin, disposable absorbent product known in the trade as "panty liner" which is fastened to the undergarment of the wearer to capture and retain the body exudate. Typically, a panty liner is constructed in the same fashion as a sanitary napkin. More specifically, it has a thin absorbent core confined into an envelope including a top, liquid-permeable layer and a bottom, liquid-impervious layer. To fasten the panty liner to the undergarment of the wearer, the liquid-impervious bottom layer is coated on selected areas with pressure-sensitive adhesive which is covered with a silicone-coated, peelable paper sheet protecting the adhesive while the panty liner is not in use. This form of construction yields an absorbent product which is efficient in providing the required protection against leakage and garment staining.

Panty liners are intended to be used much more frequently than sanitary napkins, sometimes on a daily basis, and for that reason, it is desirable to manufacture the product at the lowest possible cost. However, most of the currently marketed products require sophisticated and complex assembly equipment and techniques which makes the objective of a very low cost product difficult to achieve.

SUMMARY OF THE INVENTION

An object of the present invention is a panty liner which is relatively simple and inexpensive to manufacture, yet capable to provide excellent protection against garment staining from non-menstrual vaginal discharges.

Another object of the invention is a method for manufacturing the aforementioned panty liner.

Another object of the invention is an apparatus for manufacturing the aforementioned panty liner.

As embodied and broadly described herein, the invention provides a disposable panty liner (for the purpose of this specification, the expression "panty liner" shall mean a sanitary product for absorbing vaginal discharges, primarily of non-menstrual nature but also suitable for light menstrual discharges, such as exudate occurring at the end or at the beginning of the menstrual period, and also suitable for light urinary discharges), comprising:

a unitary sheet of non-woven fabric (for the purpose of this specification "non-woven fabric" shall mean a material having a fibrous identity whose individual fibers have been entangled by fluid forces applied to the fibers through a fluid-permeable structure which conditions and regulates the fluid forces, whereby the fluid forces mechanically interlock the fibers to form a unitary structure having a predetermined pattern) constituting a primary liquid-retaining component of said panty liner; and a liquid-impervious barrier layer on said unitary sheet of non-woven fabric for preventing body exudate collected by said unitary sheet of non-woven fabric to egress through a garment facing side of said panty liner.

In a preferred embodiment, the top surface of the non-woven fabric sheet which constitutes the skin-contacting surface of the panty liner (in this specification "skin-contacting surface" shall mean the surface of the panty liner which contacts the perineal region of the user when the panty liner is being worn) is provided with recesses in a spaced apart relationship forming discrete pockets for retaining highly viscous body exudate discharged on the panty liner. The recesses enhance the comfort potential of the product by allowing the body exudate to accumulate away from the interface between the perineal region of the wearer and the panty liner in order to diminish the sensation of wetness developed on the skin of the wearer.

Most preferably, binder is applied to the non-woven fabric sheet in order to reinforce its structure and prevent loss of integrity under the mechanical stresses exerted on the panty liner during normal usage, such as the repeated bending and twisting occurring when the person wearing the panty liner is walking. The binder is applied on the garment facing surface of the non-woven fabric sheet to maintain the top, skin contacting surface soft and fluffy for an increased comfort. However, a small amount of binder is allowed to migrate to the skin contacting surface to avoid surfacial delamination and fuzziness of the fibrous network.

In a preferred embodiment, the liquid-impervious barrier layer is constituted by a thin web of plastic material such as polyethylene, which is provided on its garment facing surface with pressure-sensitive adhesive to releasably retain the panty liner to the undergarment of the wearer. The adhesive coating is protected by a peelable silicone-coated paper sheet which is removed to expose the adhesive immediately before the panty liner is installed in the crotch portion of the undergarment.

In a first variant, the liquid-impervious barrier layer is formed solely by an adhesive coating which also serves the purpose of retaining the panty liner to the undergarment of a wearer.

In a second variant, a lightweight non-woven web having hydrophobic properties is used for making the liquid-impervious barrier layer.

As embodied and broadly described herein, the invention also provides a method for manufacturing a panty liner, said method comprising the steps of:

providing a non-woven fabric;

cutting said non-woven fabric to form a primary liquid-retaining component for said panty liner; and providing said primary liquid-retaining component with a liquid-impervious barrier layer to prevent body exudate captured by said primary liquid-retaining component to egress from a garment facing side of said panty liner.

In a preferred embodiment, the non-woven fabric is manufactured by subjecting fibrous starting material in sheet form whose individual fibers are capable of movement relatively to one another under the influence of applied fluid forces, to a fluid stream for entangling and mechanically interlocking the fibers to form a unitary reticular network. The fibrous starting material is confined between a hollow drum and a screen belt in overlapping relationship with the hollow drum, while being subjected to the influence of the fluid stream. The hollow drum has a perforated shell defining a predetermined pattern of fluid passages which condition the fluid stream to form the non-woven fabric with recesses for collecting body exudate.

The non-woven fabric is consolidated by the application of binder and it is then laminated with a polyethylene web forming the liquid-impervious barrier layer. Subsequently, the polyethylene web is coated with pressure-sensitive adhesive and covered with a silicone-coated paper web to preserve the adhesive while the panty liner is not used. The resulting laminated structure is die-cut into individual panty liners.

As embodied and broadly described herein, the invention also provides an apparatus for manufacturing panty liners from fibrous starting material in sheet form whose individual fibers are capable of movement under the influence of applied fluid forces, said apparatus comprising:

means to generate a fluid stream applied to said starting material for entangling said fibers to form a unitary, non-woven fabric;

means for applying to a first main surface of said non-woven fabric a binder to increase a resistance of said non-woven fabric;

means for providing on said non-woven fabric a liquid-impervious barrier layer to prevent body exudate discharged on a second main surface of said non-woven fabric to freely egress said first main surface;

means for applying a coating of adhesive to a main surface of said liquid-impervious barrier layer, which is opposite to said non-woven fabric in order to releasably retain said panty liner to undergarment material;

means for applying on said coating of adhesive a removable protective web for protecting said coating of adhesive while said panty liner is not in use; and means for cutting said non-woven fabric, said liquid-impervious barrier layer and said removable protective web into individual panty liners.

BRIEF DESCRIPTION OF THE DRAWINGS

The file of this application contains at least one drawing executed in color. Copies of this patent with color drawings will be provided by the Patent and Trademark Office upon request and payment of the necessary fee.

DESCRIPTION OF PREFERRED EMBODIMENTS

Figure 1:
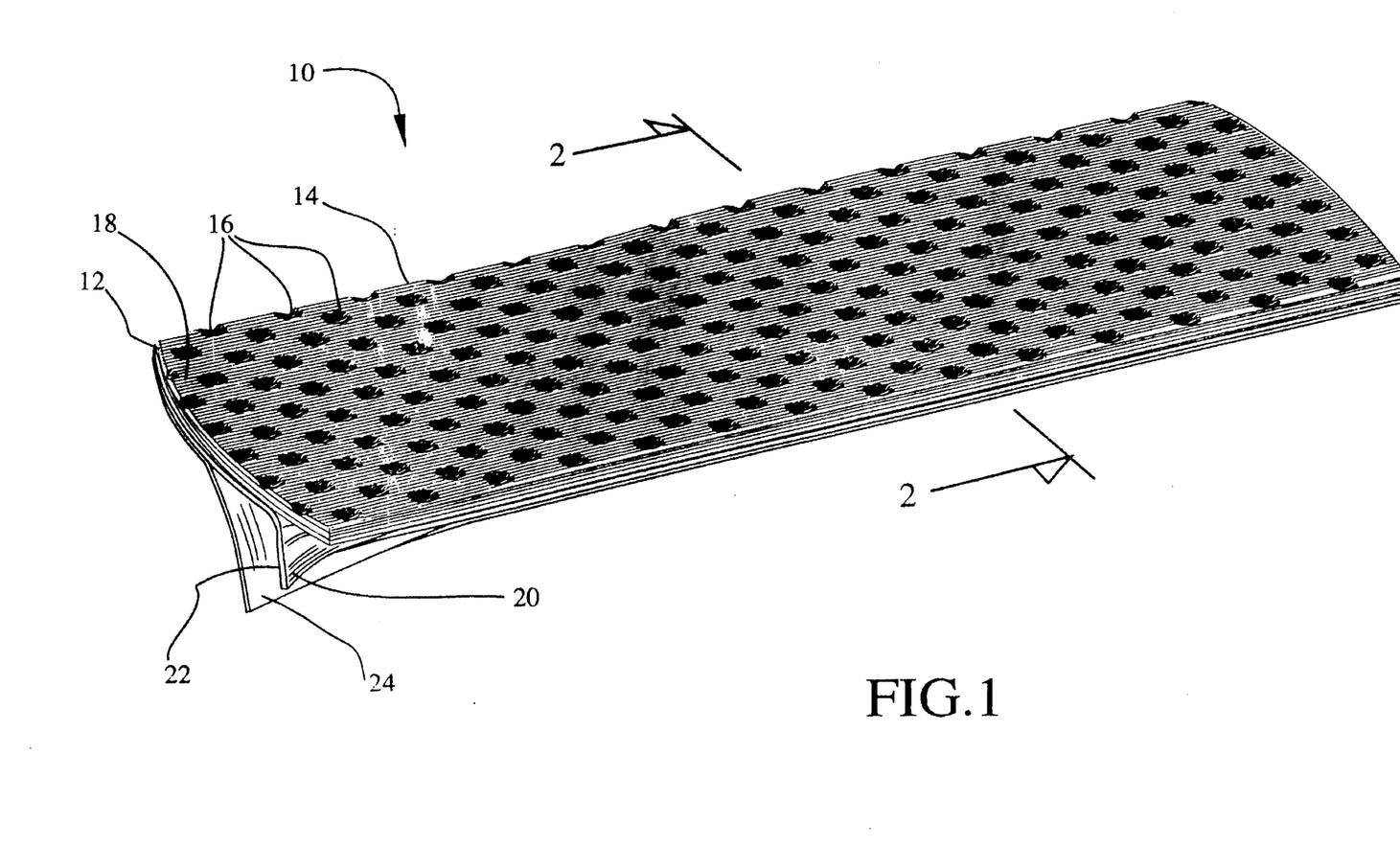
FIG. 1 is a perspective view of a panty liner constructed in accordance with the present invention.
Figure 2:
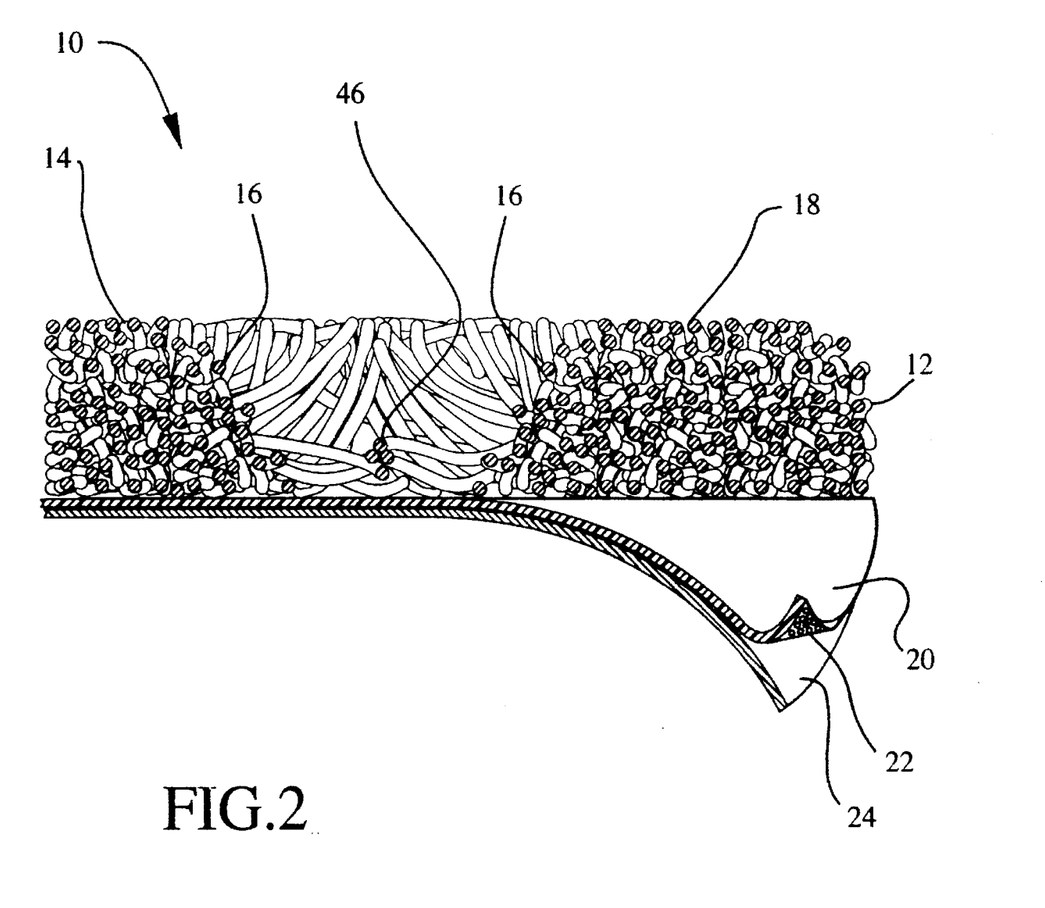
FIG. 2 is a highly enlarged cross-sectional view taken along lines 2—2 in FIG. 1.
Figure 3:
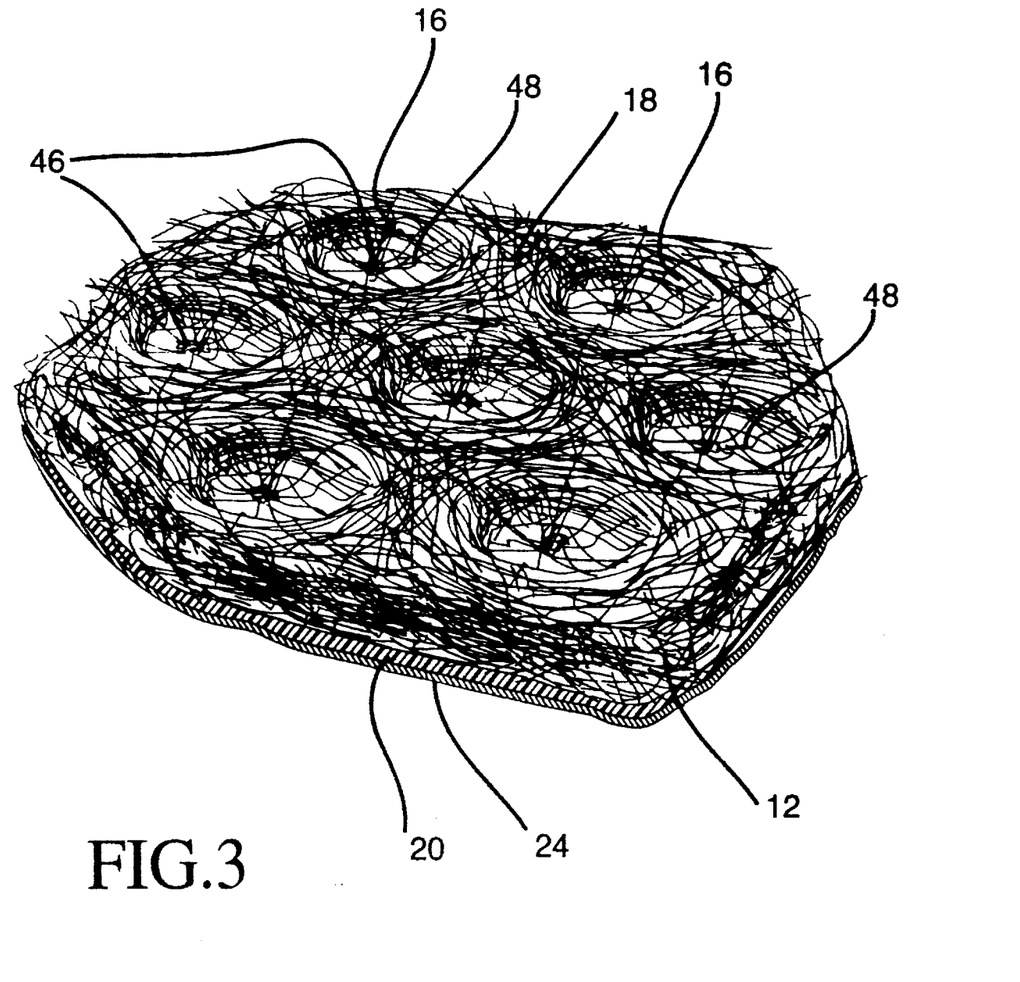
FIG. 3 is a further enlarged, fragmentary, perspective view of the panty liner in accordance with the invention, illustrating the topography of the skin-contacting surface.

FIGS. 1, 2 and 3 of the annexed drawings illustrate a non-woven panty liner constructed in accordance with the present invention. The panty liner, designated comprehensively by the reference numeral 10, comprises a unitary sheet 12 made of a non-woven fabric constituting the principal liquid-retaining component of the panty liner 10. The sheet 12 has a thickness in the range from about 0.75 mm to about 1.75 mm measured at 0.345 Kilopascals (Kpa) pressure, and preferably of about 1.35 mm. The basis weight of the sheet 12 varies in the range from about 80 grams per meter squared (g/m$^2$) to about 160 g/m$^2$. Preferably, the basis weight of the sheet 12 is of about 122 g/m$^2$.

On the top surface 14 of the layer 12, which forms the skin contacting surface of the panty liner 10, are provided a plurality of equidistant recesses 16 arranged relative to one another according to a staggered pattern. The recesses have a depth in the range from about 0.05 mm to about 1.30 mm and preferably of about 1.0 mm. The density of the recesses 16 (i.e. the number of recesses 16 per square centimeter of the surface 14) is of about 7.13 and the average diameter of the recesses 16 is of approximately 2.3 mm.

The surface configuration of the non-woven fabric sheet 12 is best shown in FIGS. 2, 3, 10 and 11. Between the recesses 16 are defined elevated land areas 18. When highly viscous, vaginal discharges are delivered on the non-woven fabric sheet 12, it has been observed that the viscous liquid has a tendency to accumulate and remain confined in the recesses 16. By virtue of the land areas 18 which contact the perineal region of the wearer, the bottom of the recesses 16 is maintained in a spaced apart relationship with the skin, thereby preventing the body exudate collected in the recesses 16 to directly contact the skin. This feature allows to increase the comfort potential of the panty liner 10.

Referring back to FIGS. 1 and 2, the garment facing side of the non-woven fabric sheet 12 is provided with a web 20 of plastic material such as polyethylene or polypropylene among others, which forms a liquid-impervious barrier layer preventing body exudate discharged on the non-woven fabric sheet 12 to egress therefrom and stain the wearer's clothes. The polyethylene web 20 is adhesively mounted to the layer 12.

On the main surface of the polyethylene web 20 which is opposite the non-woven fabric sheet 12 is provided a layer of pressure-sensitive adhesive 22 used for removably fastening the panty liner 10 to the undergarment of the wearer. In the example illustrated in the drawings, a uniform adhesive coating is depicted. However, it may be envisaged to apply adhesive to discrete areas of the polyethylene web 20, in the form of strips or bands for example, as it is well known to the person skilled in the art.

To protect the adhesive layer 22 while the panty liner 10 is not in use, a silicone-coated layer of paper material 24 covers the adhesive layer 22. As it is well-known to those skilled in the art, the protective layer 24 is peeled away to expose the adhesive in order to fasten the panty liner 10 to the undergarment of the wearer.

Figure 4:
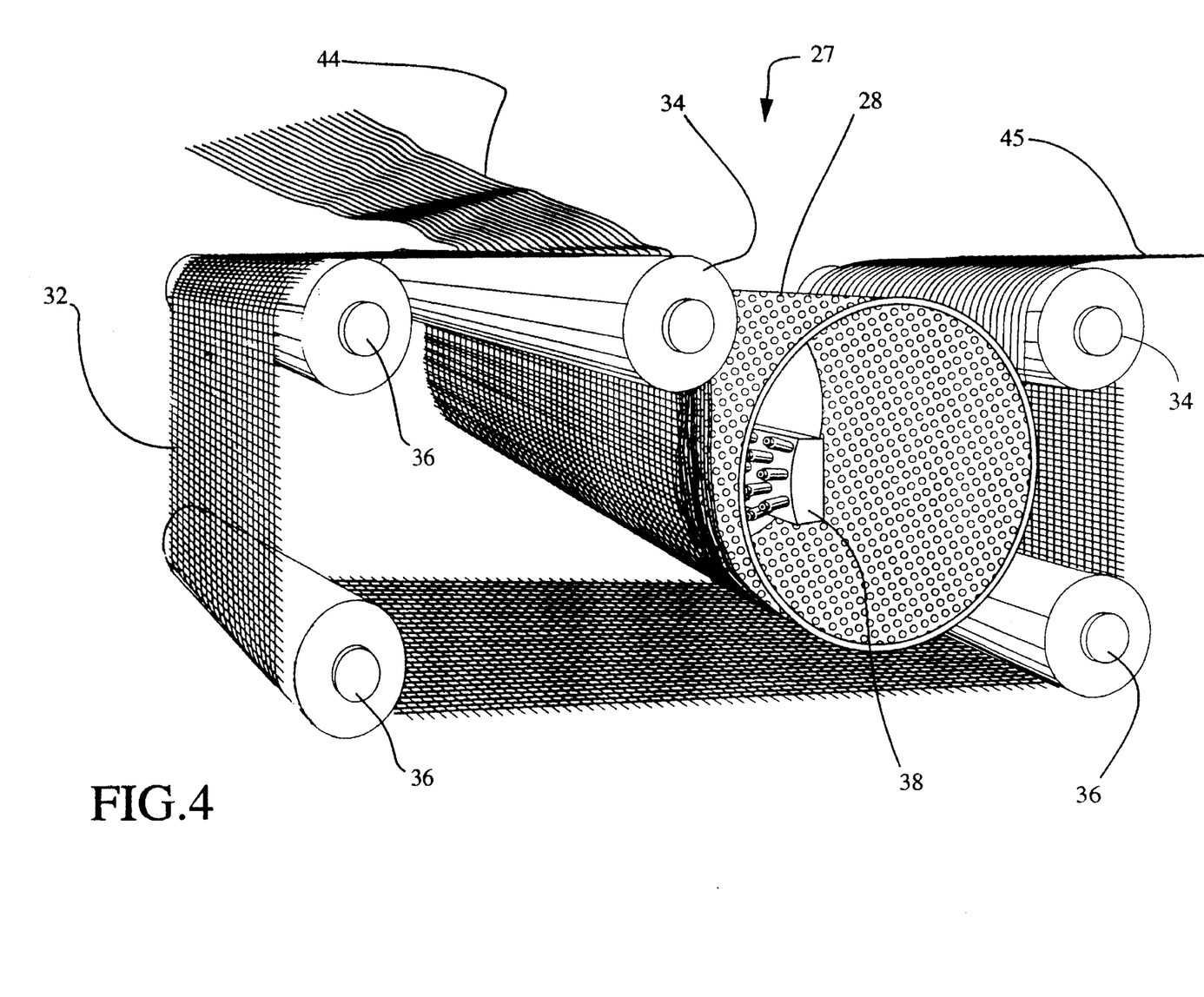
FIG. 4 is an perspective view of a fiber entangling station producing a non-woven fabric which is used as starting material for the manufacture of panty liners in accordance with the invention.
Figure 5:
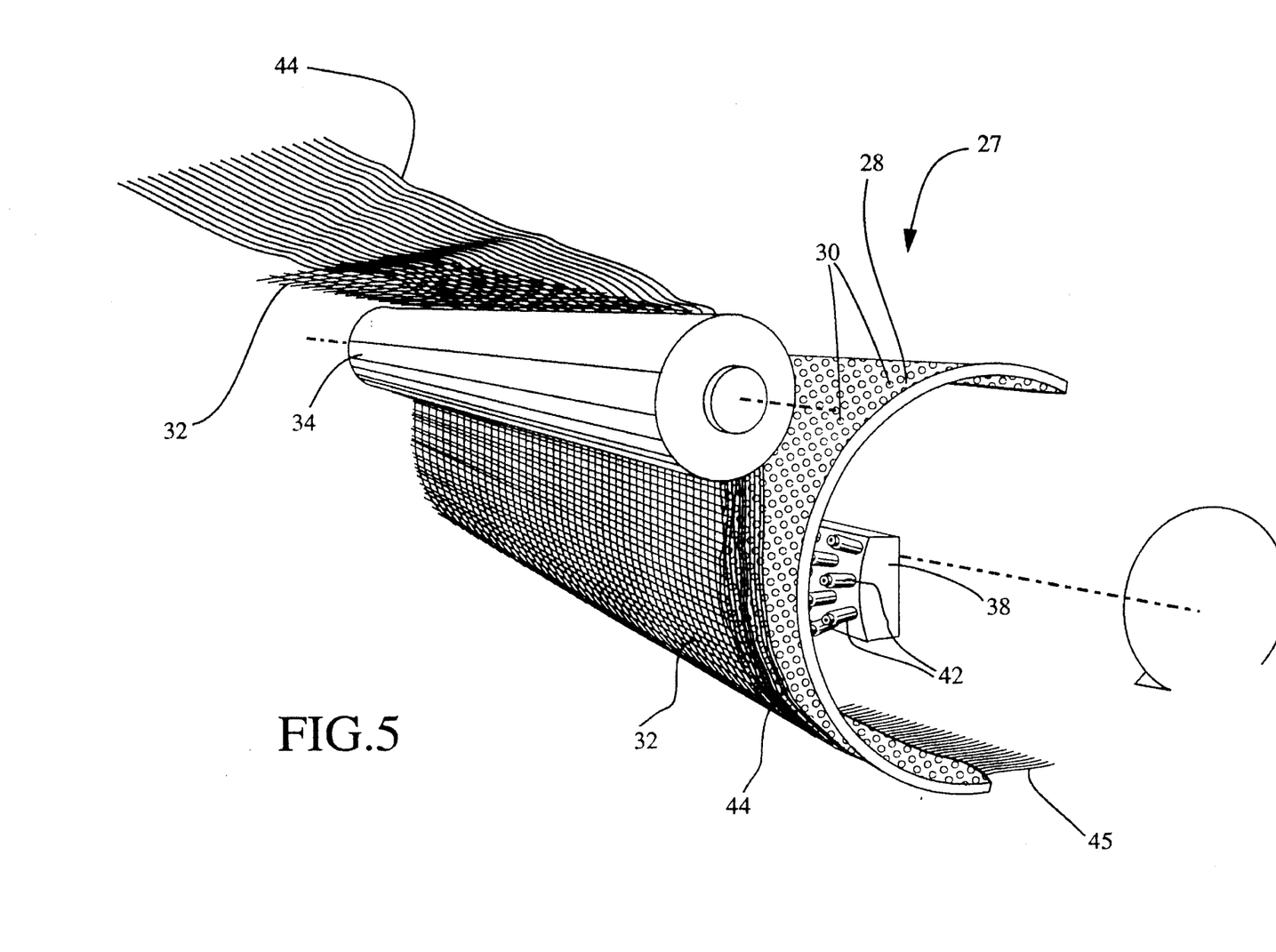
FIG. 5 is an enlarged, fragmentary, perspective view of the fiber entangling station shown in FIG. 4.
Figure 6:
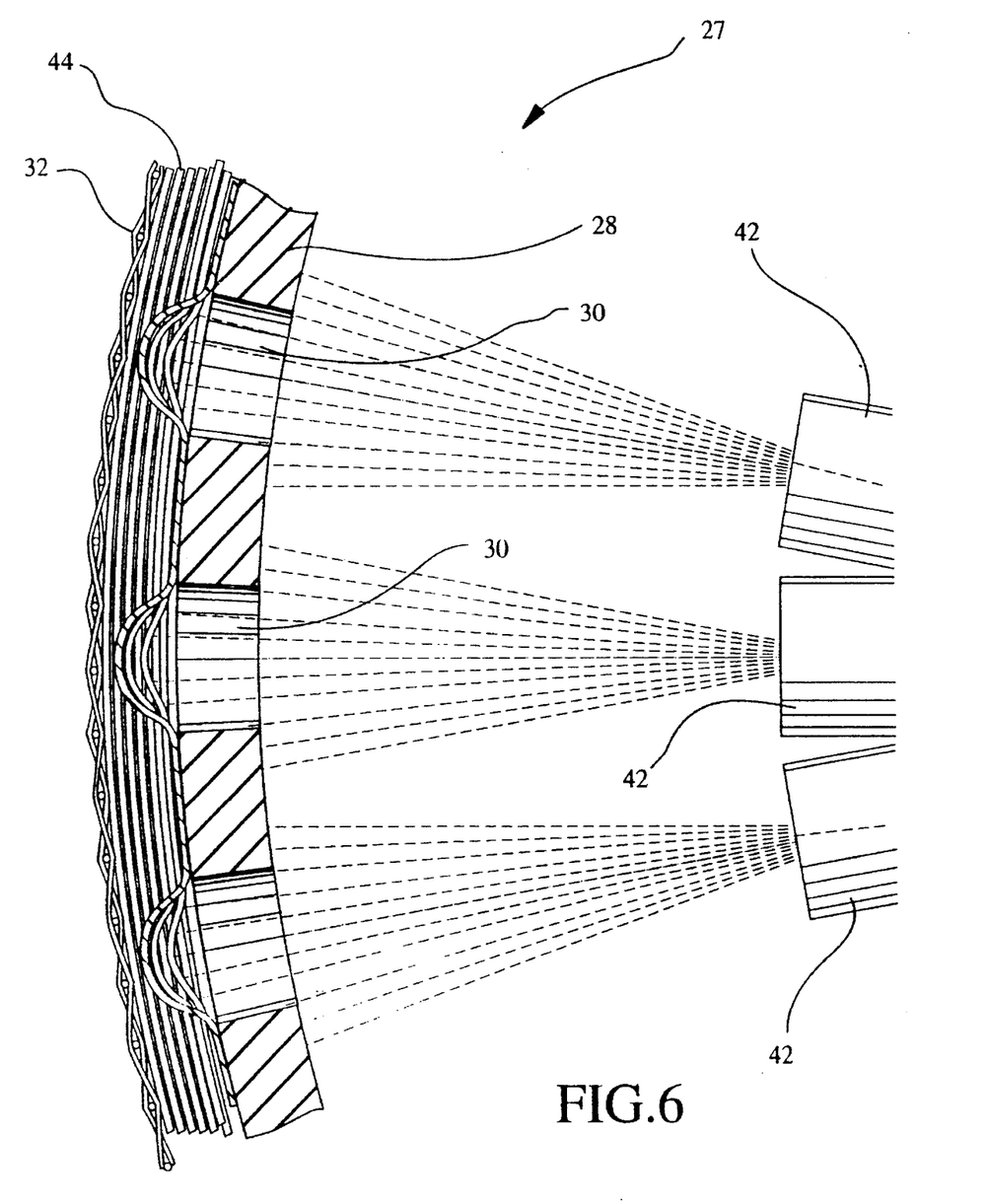
FIG. 6 is a further enlarged, fragmentary, vertical cross-sectional view of the fiber entangling station shown in FIGS. 4 and 5.

FIGS. 4 to 9 and 12 and 13 illustrate the various stations of an assembly line for manufacturing the panty liner 10. FIGS. 4 to 6 show a fiber entangling station, identified comprehensively by the reference numeral 27, producing the non-woven fabric which forms the liquid-retaining sheet 12, by the application of fluid forces to a web of starting material in sheet form in which the individual fibers are loosely associated and are free to move one relatively to the other. The fiber entangling station 27 comprises a hollow metallic drum 28 mounted for rotation about its longitudinal axis into a suitable cradle (not shown). A drive mechanism (not shown) is provided to rotate the drum 28 in a counterclockwise direction at a controlled speed. The drive mechanism is of a well-known construction and does not form part of this invention.

The shell of the drum 28 is provided on its entire surface with openings 30 arranged into a pattern which determines the distribution of the recesses 16 on the non-woven fabric sheet 12. In a most preferred embodiment, the drum 28 has a staggered pattern of equidistant and circular apertures 30, having a diameter of 2.29 mm and a concentration of 7.13 apertures per $cm^2$ which provides a 30% open area.

The fiber entangling station 27 also comprises an endless screen belt 32 which is mounted in a partially overlapping relationship with the drum 28 by means of guide rollers 34. Support rollers 36 are positioned at the corners of an imaginary rectangle and act, in conjunction with guide rollers 34, to tension and establish a path of travel for the screen belt 32. One or more of the rollers 34 and 36 are drive rollers for advancing the belt 32 in unison with the drum 28.

The screen-belt 32 is made of crossing polyester strands defining therebetween square-shaped apertures of a 23.9 mesh size, collectively providing a 55% open area.

A manifold 38 located within the hollow drum 28 produces water jets for entangling and mechanically interlocking the loosely associated fibers confined between the drum 28 and the screen belt 32 into a unitary, thin reticular network. The manifold 38 constitutes a water supply rail feeding and supporting a series of water nozzles 42 which create a plurality of closely spaced liquid streams impinging on the inner surface of the hollow drum 28. The number of nozzles 42 jetting liquid against the inner face of the drum 28 depends on the amount of energy per unit of time or power that must be supplied to the web 44 in order to entangle and mechanically interlock its fibers. The power requirement of the entangling station 27 depends on several factors, such as dimensions of the web 44, the feed rate of the web and the type of fibers which are being used, among others.

Nozzles 42 of a 15–10 size have been found satisfactory. As it is well known to those skilled in the art, the first numeral of the nozzle size refers to the spread angle of the spray produced by the nozzle while the second numeral is ten times the flow rate of the nozzle expressed in U.S. gallons per minute at a pressure of 40 pounds per square inch gage (psig).

Although not shown in the drawings, it is to be understood that the manifold 38 is connected to a source of water for producing the liquid streams. A water supply pressure of 1551 Kpa has been found satisfactory.

The operation of the fiber entangling station 27 is described hereinafter. A web 44 of starting material, containing loosely associate fibers, thus capable of movement one relatively to the other, is supplied in a continuous sheet form from a supply station (not shown) and is deposited over the horizontally extending forward run of the screen belt 32 preceding the section of the screen belt which loops the hollow drum 28. The web 44 is drawn between the hollow drum 28 and the screen belt 32, which form in combination a liquid-permeable, web confining and supporting structure, guiding and advancing the web 44 through the water streams produced by the nozzles 42.

The type of fibers used in the web 44 can vary according to the intended application. In a specific example, the web 44 is a blend comprising 80% by weight of rayon fibers and 20% by weight of polyester fibers. Alternatively, the rayon fibers may be blended with polypropylene fibers, cotton fibers, acrylic fibers, wood pulp fibers, bico fibers, paper fragments or a mixture thereof, provided in a range from about 20% to about 40% by weight of the web 44. The selected additive and the rayon fibers are admixed in desired proportions and carded to form the web 44 which is then processed at the entangling station 27. However, if it is desired to admix paper fragments with the rayon fibers a different process is required. More particularly, a continuous sheet of paper material is superposed to the web 44 and it is concurrently fed therewith in the fiber entangling station 27. The liquid streams jetted by the nozzles 42 shred the paper material and intersperse the resulting fragments through the fibrous matrix.

FIG. 6 illustrates in a detailed manner the mechanism of fluid formation providing a non-woven fabric 45 well-suited for use in manufacturing the primary liquid-retaining component of the panty liner 10. The body of water discharged by the nozzles 42 impinges against the inner surface of the hollow drum 28 and it is transformed into columnar water streams, whose shape and distribution correspond to the shape and distribution of the openings 30. The water streams exert rearranging forces moving the fibers laying across the drum openings 30 laterally, packing the fibers on the land areas of the drum to create a first pattern in the non-woven fabric 45 rendering the recesses 16.

The fine screen-belt 32, in overlapping relationship with the web 44 of starting material, further conditions the water streams by forcing the water drops to pass in the apertures defined by the crossing polyester strands. In turn, the moving water particles draw in those apertures the fibers near the bottom of the recesses 16, which are packed into one or more knobs interconnected to the adjoining fibrous network by fiber bundles.

Figure 10:
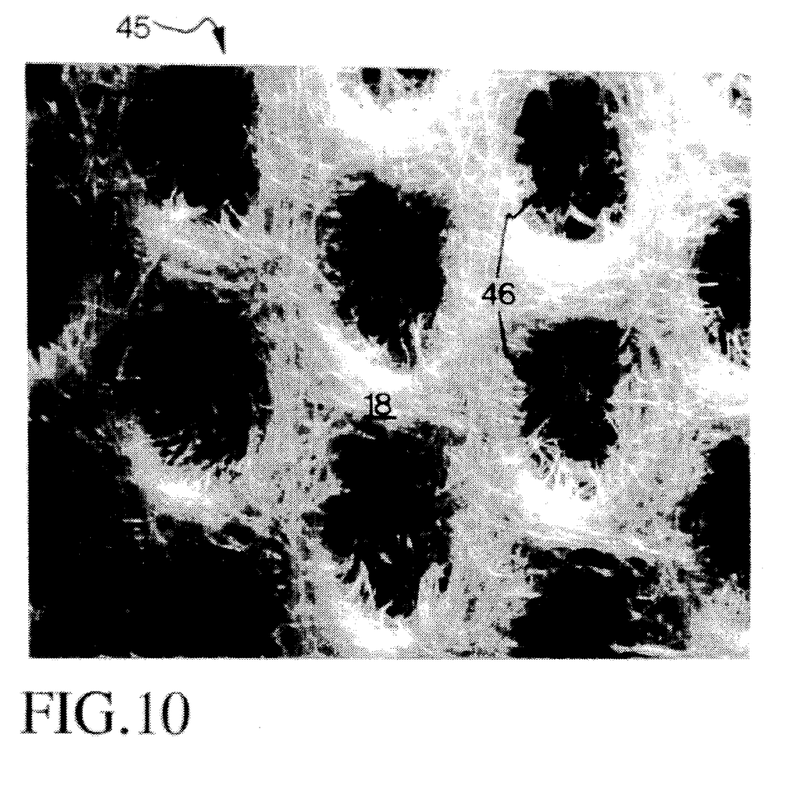
FIG. 10 is a microphotograph of a non-woven fabric in plan view, manufactured by the fiber entangling station shown in FIGS. 4, 5 and 6.
Figure 11:
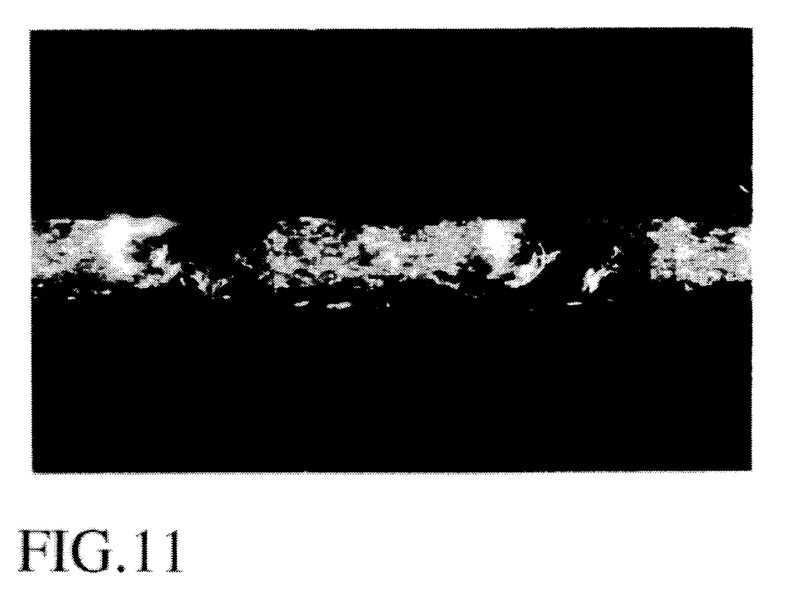
FIG. 11 is a microphotograph of the non-woven fabric in cross-sectional view, manufactured by the fiber entangling station shown in FIGS. 4, 5 and 6.

The resulting non-woven fabric structure, as best shown in FIGS. 10 and 11, has two distinct patterns. The first pattern, corresponding to the recesses 16, extends throughout the entire surface of the non-woven fabric 45 and exhibits a series of low fiber density areas corresponding in shape and distribution to the apertures 30 on the drum 28. The second pattern is discontinuous and it is formed in the low fiber density areas of the first pattern, being characterized by one or more knobs 46 interconnected by fiber bundles 48.

More specifically, the non-woven fabric 45 is characterized by a basis weight of about 122 $g/m^2$, a thickness of 1.35 mm measured at 0.345 Kpa. The recesses 16 have a depth of about 1.0 mm, an average diameter of 2.3 mm and a density (i.e. number of recesses per unit area of the non-woven fabric 45) of about 7.13 per $cm^2$.

Further details on the principle for manufacturing a non-woven fabric by fluid entanglement can be found in the prior art. At the end, example may be had to the following Canadian patents granted to Johnson & Johnson, U.S.A. which constitute references of interest to the present subject. The subject matter of these patents is incorporated herein by reference.

| CANADIAN PATENTS | ISSUE DATES |
| --- | --- |
| 915,398 | November 28, 1972 |
| 915,397 | November 28, 1972 |
| 915,398 | November 28, 1972 |
| 915,399 | November 28, 1972 |
| 915,400 | November 28, 1972 |
| 915,401 | November 28, 1972 |
| 915,402 | November 28, 1972 |
| 915,403 | November 28, 1972 |
| 915,408 | November 28, 1972 |
| 1,143,929 | April 5, 1983 |

Figure 7:
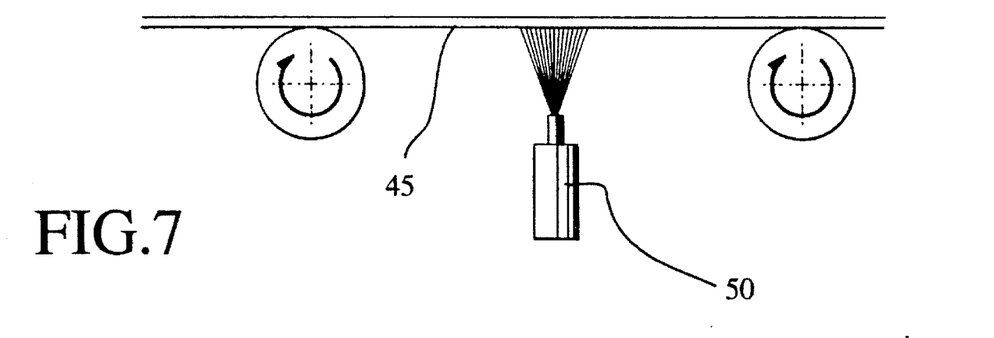
FIG. 7 is schematical view of a binder applicator station located downstream of the fiber entangling station, to apply binder to the undersurface of the non-woven fabric.
Figure 8:
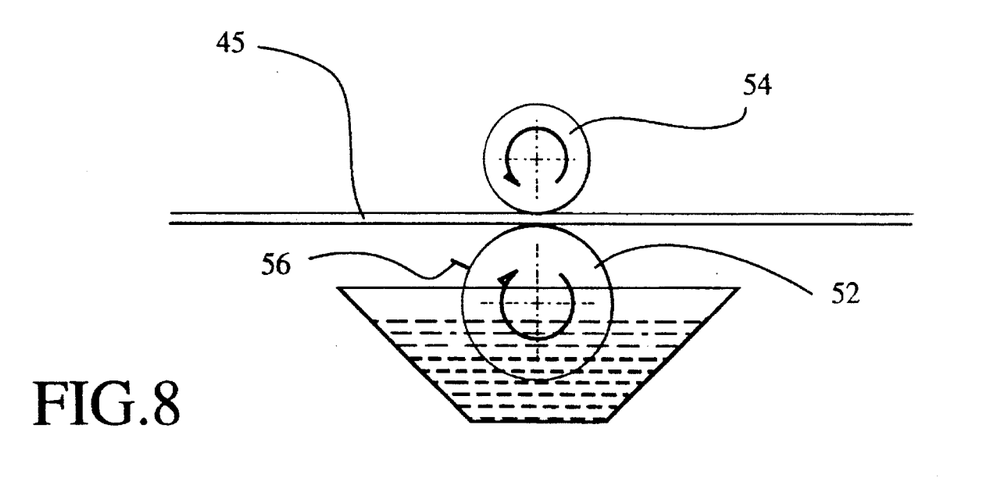
FIG. 8 is a schematical view of a binder applicator station according to a variant.
Figure 9:
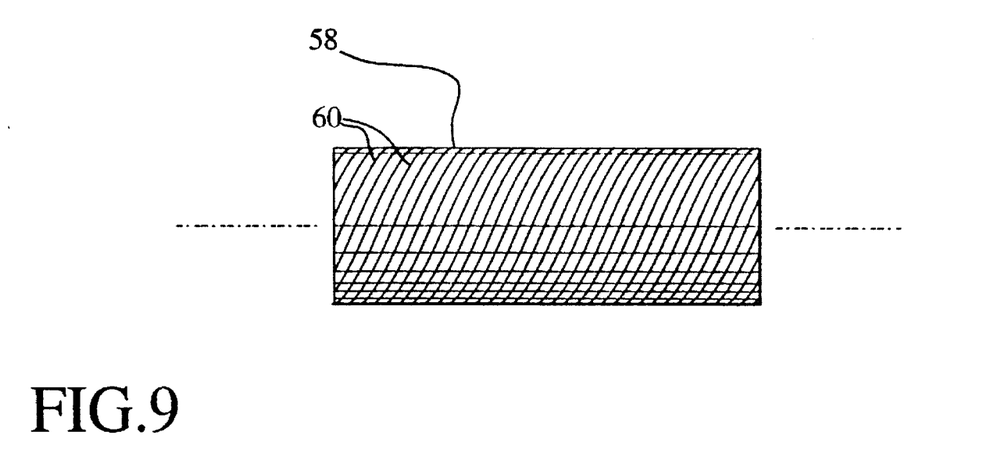
FIG. 9 is an elevational view of a binder applicator roll to deposit binder on the non-woven fabric according to a predetermined pattern.

As shown in FIGS. 7, 8 and 9, downstream of the fiber entangling station 27, the apparatus according to the invention comprises a binder applicator station which applies a solution of binder to the non-woven fabric 45. The binder, when cured, solidifies and consolidates the non-woven fabric 45, increasing its resistance. Binders are commercially available compounds and the selection of a particular binder depends upon the desired characteristics of the final product. The following binders have been found satisfactory:

vinyl ethylene;

vinyl chloride;

vinyl acetate;

vinyl acrylate polyvinyl alcohol;

polyvinyl acetate;

carboxylated polystyrene;

rubber polyethylene;

polyacrylonitrile; and mixtures thereof.

The binder applicator station may take several forms. As shown in FIG. 7, the binder may be sprayed directly onto the non-woven fabric 45 by a nozzle 50 in fluid communication with a supply of liquid binder under pressure (not shown in the drawings).

In a variant shown in FIG. 8, the binder applicator station comprises a smooth-surfaced coating roll 52 having a lower end immersed in a binder bath. A back-up roll 54 is provided above the roll 52 to define therewith a nip through which the non-woven fabric 45 passes. As the roll 52 rotates a thin film of binder adheres thereto which is deposited on the non-woven fabric 45 through rolling contact therewith. A scraper blade 56 is provided to control the thickness of the binder film adhering to the surface of the coating roll 52.

The smooth-surfaced coating roll 52 and the nozzle 50 will achieve a uniform binder deposition, which is acceptable for some applications. However, it is preferred to apply the binder according to a pattern of parallel lines which has the advantage of sufficiently consolidating the non-woven fabric 45 without stiffening the fibrous network to the point where it becomes uncomfortable to wear. To achieve the desired binder deposition pattern, a coating roll having a relief surface is required, the recessed areas of the relief surface constituting the binder transfer surfaces. An example of such roll, identified by the reference numeral 58 is shown in FIG. 9. The circumferential surface of the roll 58 is machined to form a multitude of oblique grooves 60, which are parallel to one another. In a most preferred embodiment, the grooves 60 have a width of 0.46 mm, a depth of 0.46 mm and a concentration (i.e. number of grooves per linear centimeter) of 13.78.

Other binder application methods are possible. For example, the binder may be deposited in a foamed condition on the non-woven fabric 45, which is then caused to penetrate therein by the application of vacuum. A binder solution can be foamed by providing therein an effective amount of surfactant and by agitating and aerating the solution.

An important aspect of the binder treatment, irrespective of the specific application method, resides in that the binder is applied on the undersurface of the non-woven fabric 45 (the surface which is opposite to the skin-contacting surface), in order to preserve the softness and the comfort of the skin-contacting surface. If the binder is applied on the other side of the non-woven fabric 45, a hard crust will be formed on the skin-contacting surface which can cause discomfort and rash.

The binder is applied in a liquid state on the underside of the non-woven fabric 45 and immediately after it is deposited thereon, the binder migrates toward the top surface under the effect of capillary pressure. The migration ceases when the binder is cured. As a result of such migration the binder concentration through the fibrous network varies across its thickness; the binder concentration is highest at the undersurface and lowest at the top surface. Such concentration gradient is highly advantageous because it allows to consolidate the undersurface region of the non-woven fabric 45 for an increased resistance to defiberization while maintaining the top, skin-contacting surface soft and fluffy which is comfortable to the wearer.

It should be noted that a small amount of binder on the skin-contacting surface of the non-woven fabric 45 is not necessarily undesirable because the binder prevents a surfacial delamination and fuzziness of the fibrous network to occur.

The amount of binder applied to the non-woven fabric 45 is important to achieve a satisfactory balance between a good resistance to defiberization on one hand without compromising the comfort potential of the non-woven fabric 45 on the other hand. Preferably, the amount of binder applied is in the range from about 8% to about 17% of solids by weight of the non-woven fabric 45 treated with binder, more preferably in the range from about 11% to about 15% and most preferably of about 12.6%.

Figure 12:
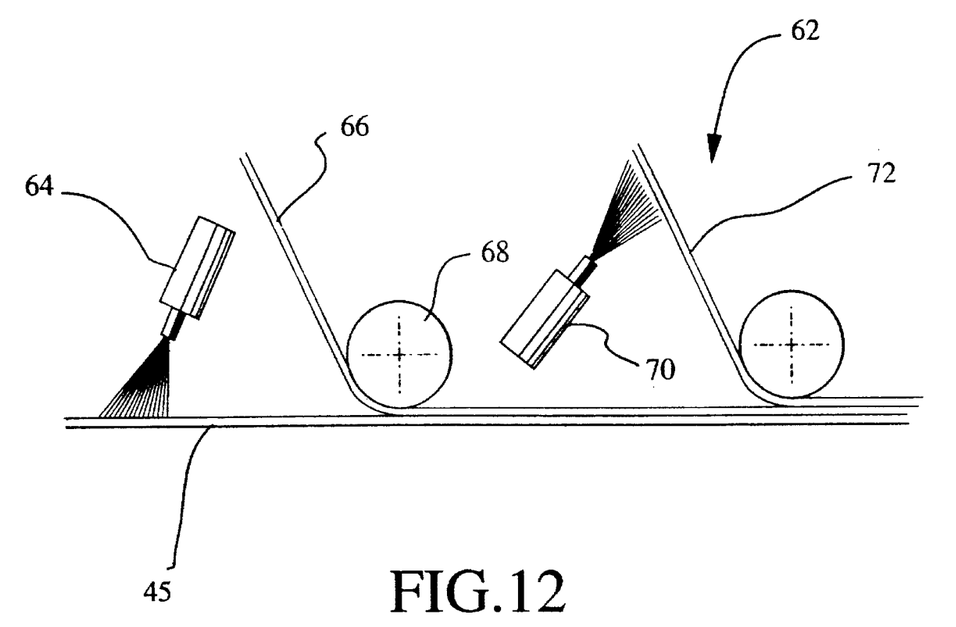
FIG. 12 is a schematical view of an assembly station for laminating the non-woven fabric with a liquid-impervious barrier layer, and for applying on the liquid-impervious barrier layer adhesive zones covered with a peelable protective sheet.

To complete the manufacture of the panty liner 10, the non-woven fabric 45 is transferred to an assembly station 62 illustrated schematically in FIG. 12. The assembly station 62 comprises a first adhesive applicator 64 in the form of a spray nozzle which sprays the non-woven fabric 45 with an adhesive. The spray pattern is adjusted to cover uniformly the non-woven fabric 45 with a thin coat of adhesive material. Downstream of the adhesive applicator 64, a thin web of polyethylene 66 which forms the liquid-impervious barrier 22, is guided and pressed by a roll 68 against the adhesive-coated surface of the non-woven fabric 45 in order to permanently bond the non-woven fabric 45 and the polyethylene web 66 together.

Downstream of the adhesive applicator 64 is provided a second adhesive spray nozzle 70 which applies a coating of pressure sensitive adhesive on a web 72 of silicone-coated paper. The silicone-coated paper web 72 is then brought in contact with the polyethylene web 66 in order to transfer the pressure sensitive adhesive to the polyethylene web 66. The adhesive adheres preferentially to the polyethylene web 66 since the paper web 72 has a non-sticky surface. Subsequently, the paper web 72 can be peeled away in order to expose the adhesive which is used for fastening the panty liner 10 to undergarment material. As it is well known to persons skilled in the art, the pressure-sensitive adhesive can be applied to the polyethylene web 66 either as a continuous uniform coating or only at discontinuous areas such as strips or bands.

Figure 13:
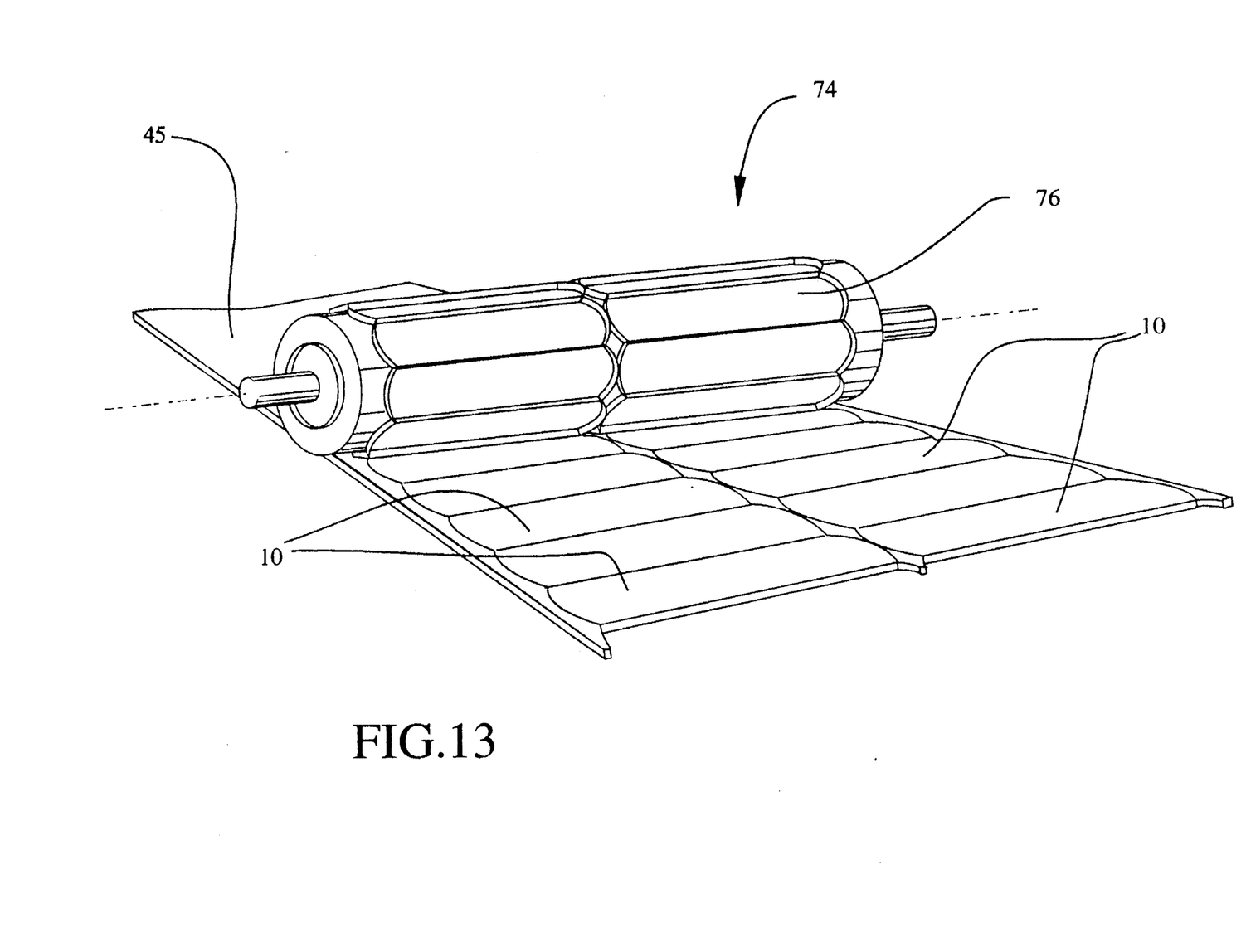
FIG. 13 is an perspective view of a station for cutting the laminated web produced by the assembly station of FIG. 12 into individual panty liners.

From the assembly station 62, the laminated web is transferred to a cutting station 74 at which all the layers of the laminated web are simultaneously cut by a rotary cutting die 76 to form individual panty liners 10.

In order to simplify the manufacturing operation of the panty liner 10, it may be envisaged to coat the non-woven fibrous web 45 with a single, continuous layer of liquid-impervious adhesive which fulfils a dual function, namely providing the liquid-impervious barrier to prevent body exudate discharged on the non-woven fabric sheet 12 to egress from a garment facing side thereof and also constituting the agency for fastening the panty liner 10 to the undergarment of the wearer. Such an embodiment is highly advantageous because it allows to eliminate the application of the polyethylene web 66 and the second adhesive applicator nozzle 70.

It is within the reach of a person skilled in the art to select the liquid-impervious adhesive necessary for manufacturing the panty liner 10 according to this variant.

Alternatively, a lightweight non-woven web treated with water repellant agent to develop hydrophobicity can be used as liquid-impervious barrier. In a specific example a hydro-entangled non-woven fabric having a basis weight of 21 g/m$^2$ and a bulk density of 0.141 g/cc has been found satisfactory. It will be plain that a non-woven fabric will have a utility as a liquid-impervious barrier only if its fibrous network is relatively tight and free of large void areas that could allow liquid to escape.

The scope of the present invention is not limited by the description, examples and suggestive uses herein as modifications and refinements can be made without departing from the spirit of the invention. Applications of the product, method and apparatus of the present invention for sanitary and other health-care uses can be accomplished by any sanitary protection, incontinence, medical and absorbent methods and techniques as are presently or prospectively known to those skilled in the art. Thus, it is intended that the present application covers the modifications and variations of this invention provided that they come within the scope of the appended claims and their equivalents.

We claim:

1. A disposable panty liner, consisting essentially of:
   a unitary sheet of non-woven fabric constituting a primary liquid-retaining component of said panty liner wherein said unitary sheet of non-woven fabric has a top surface constituting a skin-contacting surface of said panty liner; and
   a liquid-impervious barrier layer on said unitary sheet of non-woven fabric for preventing body exudate collected by said unitary sheet of non-woven fabric to egress through a garment facing side of said panty liner, wherein said top surface comprises a plurality of recesses in a spaced apart relationship, said recesses being capable to retain highly viscous body exudate discharged on said panty liner.

2. A panty liner as defined in claim 1, wherein said recesses have a depth in the range from about 0.05 mm to about 1.30 mm.

3. A panty liner as defined in claim 1, wherein said recesses have a depth of about 1.0 mm.

4. A panty liner as defined in claim 1, wherein said unitary sheet of non-woven fabric has a thickness in the range from about 0.75 mm to about 1.75 mm measured at a 0.345 Kpa pressure.

5. A panty liner as defined in claim 1, wherein said unitary sheet of non-woven fabric has a thickness of about 1.35 mm measured at a 0.345 Kpa pressure.

6. A panty liner as defined in claim 1, wherein said unitary sheet of non-woven fabric has a basis weight in the range from about 80 g/m$^2$ to about 160 g/m$^2$.

7. A panty liner as defined in claim 1, wherein said unitary sheet of non-woven fabric has a basis weight of about 122 g/m$^2$.

8. A panty liner as defined in claim 1, wherein said liquid-impervious barrier layer is discrete from said unitary sheet of non-woven fabric and affixed to a bottom surface thereof.

9. A panty liner as defined in claim 8, wherein said liquid-impervious barrier layer includes a layer of plastic material.

10. A panty liner as defined in claim 8, wherein said liquid-impervious barrier layer includes a layer of non-woven fabric.

11. A panty liner as defined in claim 8, wherein said liquid-impervious barrier layer includes a coating of liquid-impervious material.

12. A panty liner as defined in claim 11, wherein said liquid-impervious material is an adhesive.

13. A panty liner as defined in claim 8, wherein said liquid-impervious barrier layer is adhesively mounted to said unitary sheet of non-woven fabric.

14. A panty liner as defined in claim 1, further comprising means for releasably mounting said panty liner to an undergarment of a wearer.

15. A panty liner as defined in claim 14, wherein said means for releasably mounting said panty liner to an undergarment of a wearer includes a coating of adhesive material affixed to said unitary sheet of non-woven fabric.

16. A panty liner as defined in claim 15, wherein said coating of adhesive material is applied to a garment facing side of said liquid-impervious barrier layer.

17. A panty liner as defined in claim 15, further comprising a removable protective medium covering said coating of adhesive material while said panty liner is not in use.

18. A panty liner as defined in claim 1, wherein said unitary sheet of non-woven fabric comprises rayon fibers.

19. A panty liner as defined in claim 18, wherein said unitary sheet of non-woven fabric comprises rayon fibers blended with an additive provided in an amount ranging from about 20% to about 40% by weight of the unitary sheet of non-woven fabric and selected from the group consisting of polypropylene fibers, cotton fibers, acrylic fibers, wood pulp fibers, bico fibers, paper fragments and mixtures thereof.

20. A panty liner as defined in claim 1, wherein said unitary sheet of non-woven fabric includes a binder substance for increasing a resistance of said unitary sheet of non-woven fabric.

21. A panty liner as defined in claim 20, wherein said binder substance is selected from the group consisting of vinyl ethylene, vinyl chloride, vinyl acetate, vinyl acrylate, polyvinyl alcohol, polyvinyl acetate, carboxylated polystyrene, rubber polyethylene, polyacrylonitrile and mixtures thereof.

22. A panty liner as defined in claim 20, wherein said binder substance is present in said unitary sheet of non-woven fabric in the range from about 8% to about 17% of solids by weight of said unitary sheet of non-woven fabric treated with binder.

23. A panty liner as defined in claim 20, wherein said binder substance is present in said unitary sheet of non-woven fabric in the range from about 11% to about 15% of solids by weight of said unitary sheet of non-woven fabric treated with binder.

24. A panty liner as defined in claim 20, wherein said binder substance is present in said unitary sheet of non-woven fabric in an amount of about 12.6% of solids by weight of said unitary sheet of non-woven fabric treated with binder.

25. A panty liner as defined in claim 20, wherein a concentration of said binder substance in said unitary sheet of non-woven fabric diminishes from a bottom surface of said unitary sheet of non-woven fabric toward a skin-contacting surface thereof.

* * * * *